April 13, 1976 A. G. STANIFORTH Plant Pat. 3,864
APPLE TREE
Filed March 13, 1975
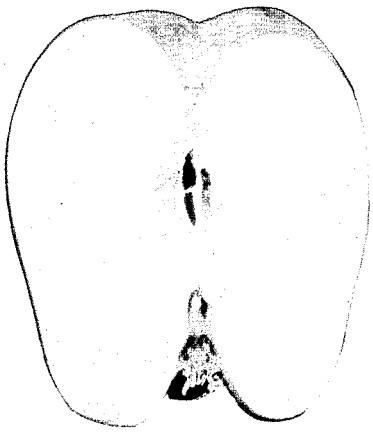
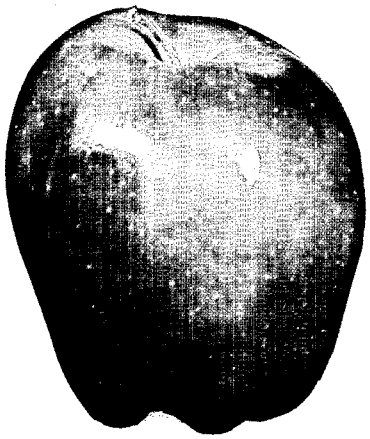
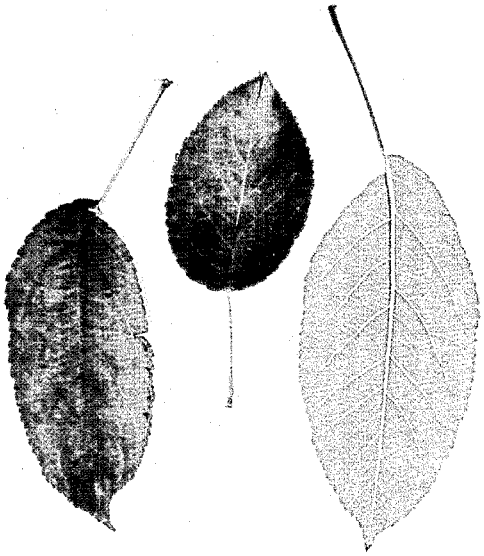
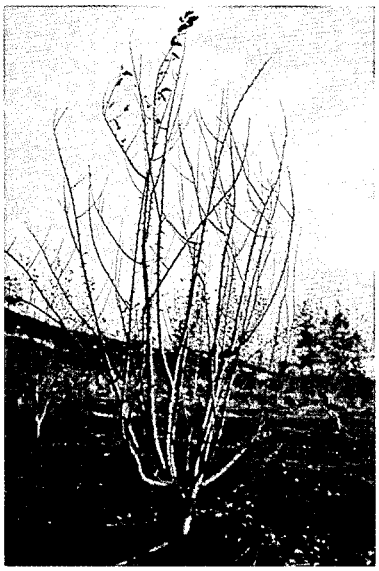

United States Patent

Plant Pat. 3,864

Patented Apr. 13, 1976

3,864

APPLE TREE

Athol G. Staniforth, Naramata, British Columbia, Canada, assignor to Columbia & Okanogan Nursery Co., Inc., Wenatchee, Wash.

Filed Mar. 13, 1975, Ser. No. 558,141

Int. Cl. A01h *5/03*

U.S. Cl. Plt—35 1 Claim

The present invention relates to a new and distinct variety of apple tree which was discovered by me as a limb sport in my cultivated orchard located at South Bench, Naramata, in the Province of British Columbia, Dominion of Canada.

At the time of my discovery aforesaid, I was growing in my orchard a block of apple trees of the variety known as "Royal Red Delicious" (U.S. Plant Pat. No. 1,278). In the course of these growing operations which were conducted under my personal care and supervision, my attention was attracted to one particular tree on which I noticed a limb sport which showed spur characteristics not found on the other limbs or on any of the other trees in my block of "Royal Red Delicious." Out of curiosity, I took budwood from this limb and grafted the same onto a young "McIntosh" tree (unpatented). Subsequently, I grafted other trees from the first graft and continued to observe and test the original sport limb and the succeeding grafted progeny derived by me therefrom through several generations. As the result thereof, I am convinced that my new sport is definitely distinguished from its parent, as well as from all other varieties of apple trees of which I am aware, as evidenced by the following unique combination of principal characteristics which are outstanding in the sport:

(1) A more columnar habit of growth than the parent variety "Royal Red Delicious," with a much greater number of fruit spurs per unit length of wood;
(2) More vigorous and lush foliage which is deeper green in color;
(3) Fruit which closely resembles that of "Royal Red Delicious" in shape, size, flesh and skin colors, including its distinctive bright cherry-red skin color and early coloring habit as an overall blush without stripes; and
(4) A later fruit-maturing habit ranging from a week to 10 days later than the fruit of "Royal Red Delicious."

Asexual reproduction of my new variety through several generations by bud-grafting, as performed by me in my orchard aforesaid in British Columbia, Canada, shows that the foregoing characteristics and distinctions come true and are established and transmitted through succeeding propagations.

The accompanying drawing shows a bare young tree of my new variety depicting its spur type habit of growth, and also shows typical foliage and fruit specimens, with one of the fruit specimens being shown in cross-section and the leaves showing both the upper and the under surfaces thereof, all as depicted in color as nearly true as it is reasonably possible to make the same in a color illustration of this character.

The following is a detailed description of my new variety, with color terminology in accordance with Ridgway's Color Standards and Nomenclature, except where general color terms of ordinary dictionary significance are obvious:

Locality where grown and observed: Naramata, British Columbia, Canada.

Dates of first and last pickings: About September 15 and about September 25, respectively, depending on seasonal conditions.

Tree: Medium size; medium vigor; upright; dense; vaseformed; slow-growing; hardy; very productive; regular bearer.

*Trunk.*—Medium stockiness; medium smoothness.

*Branches.*—Medium thickness; smooth; much-branched. Color—Gray-green.

*Lenticels.*—Medium number; small.

Foliage:

*Leaves.*—Large; long (from about 4 inches to 4½ inches); medium wide (from about 1½ inches to 2 inches); ovate; abruptly pointed; medium thickness; rugose, Color.—Dark green. Margin.—Crenate; finely serrate. Petiole.—Medium long (about ¾ inch); medium thickness.

Flowers: Similar to "Royal Red Delicious."

*Dates of first and full bloom.*—About April 27 and May 4, respectively.

*Size.*—Large.

*Color.*—Pink.

Fruit:

*Maturity when described.*—About September 25.

*Size.*—Variable. Axial diameter—About 2½ inches. Transverse diameter—About 3 inches.

*Form.*—Uniform; unsymmetrical; irregular; oblong-conical; slightly ribbed.

*Cavity.*—Symmetrical; flaring toward apex; sometimes furrowed; pubescent toward apex. Depth—About ¾ inch. Breadth—About ½ inch.

*Basin.*—Symmetrical; abrupt; flaring; wide base; furrowed; pubescent.

*Stem.*—Medium caliper; pubescent; bracts wanting. Length—About 1 inch.

*Calyx.*—Nearly closed; segments persistent, broadly acute; about 5/16 inch long; erect; apex converged from base toward center; outer surface glabrous; inner surface pubescent.

*Eye.*—Medium size; partially closed.

*Skin.*—Medium thickness; tough; smooth; glossy; waxed. Dots—Conspicuous; small; even; depressed; circular. Color—whitish. Distribution—Uniform. Ground color—Bright, shiny red overall blush without stripes. Bloom—Abundant. Scarf-skin—Light gray. General color effect—Carmine, Plate I in the darkest areas and shading out to near Eugenia Red, Plate XIII, with some lighter areas.

*Flesh.—Juicy.* Color—White, with yellowish tint. Texture—Firm; tender; fine; crisp. Flavor—Mild; rich. Aroma—Distant. Quality—Best. Core—Distant.

*Bundle area.*—Medium size; broadly ovate; symmetrical.

*Halves of core.*—Equal.

*Bundles.*—Conspicuous; in one whorl. Color—Yellowish.

*Alternate bundle.*—Reaches tube above stamens.

*Core lines.*—Meeting; distinct in cross-section.

*Carpellary area.*—Distinct; from small to medium size.

*Calyx tube.*—Pubescent; broadly conical. Stem of funnel—Long. Depth of tube to shoulder—About ¾ inch. Entire depth—About 1 inch.

*Stamens.*—In two whorls; median.

*Axillary cavity.*—Wanting.

*Seed cells.*—Closed.

*Cell walls.*—Thick; tough. Length—About 1 inch. Breadth—About 1½ inches.

*Longitudinal section.*—Obovate; acute at apex.

*Surface.*—Smooth.

*Cross section.*—Narrow.

Seeds: 7 perfect; 1 imperfect; usually not more than 2 in one cell.

*Length.*—From about 3/16 inch to ¼ inch.

*Breadth.*—From about ⅛ inch to 3/16 inch.

*Form.*—Obtuse.
*Color.*—Brown.

Use: Market; dessert.

Keeping quality: Good; about 140 days in ordinary storage.

Disease and insect resistance: Good resistance to insects and diseases to which apple trees are usually subject, as determined from comparison with other varieties grown under the same conditions at Naramata, B.C., Canada.

I claim:

1. A new and distinct variety of apple tree, substantially as herein shown and described, characterized particularly as to novelty by the unique combination of a more columnar habit of growth than the parent variety "Royal Red Delicious," with a much greater number of fruit spurs per unit length of wood; more vigorous and lush foliage which is deeper green in color; fruit which closely resembles that of "Royal Red Delicious" in shape, size, flesh and skin colors, including its distinctive bright cherry-red skin color and early coloring habit as an overall blush without stripes; and a later fruit-maturing habit ranging from a week to 10 days later than the fruit of "Royal Red Delicious."

No references cited.

ROBERT E. BAGWILL, Primary Examiner